United States Patent [19]

Tocker

[11] 4,399,122

[45] Aug. 16, 1983

[54] CONTROLLED RELEASE GRANULES

[75] Inventor: Stanley Tocker, Wilmington, Del.

[73] Assignee: E. I. Du Pont de Nemours and Company, Wilmington, Del.

[21] Appl. No.: 315,304

[22] Filed: Oct. 27, 1981

Related U.S. Application Data

[63] Continuation-in-part of Ser. No. 114,729, Feb. 7, 1980, abandoned, which is a continuation-in-part of Ser. No. 18,528, Mar. 8, 1979, abandoned.

[51] Int. Cl.$^3$ ............... A61K 31/765; A61K 31/775; A61N 25/26; A61N 25/34
[52] U.S. Cl. .............................. 424/21; 424/24; 424/82
[58] Field of Search ............................ 424/21, 24, 82

[56] References Cited

U.S. PATENT DOCUMENTS

| | | | |
|---|---|---|---|
| 3,074,845 | 1/1963 | Geary | 424/82 |
| 3,366,539 | 1/1968 | Woodbury | 424/218 |
| 3,530,220 | 9/1970 | Buchanan | 424/320 |
| 3,740,419 | 6/1973 | Campbell | 424/21 |
| 4,032,654 | 6/1977 | Corty | 424/327 |

FOREIGN PATENT DOCUMENTS

| | | |
|---|---|---|
| 846785 | 7/1970 | Canada . |
| 1542449 | 3/1979 | United Kingdom . |

*Primary Examiner*—Stanley J. Friedman

[57] ABSTRACT

Controlled release granules of methyl 2-(dimethylamino)-N-[[(methylamino)carbonyl]oxy]-2-oxo-ethanimidothioate, oxamyl, are effective soil insecticides and nematicides, and are especially useful for the prolonged control of root knot nematodes.

9 Claims, No Drawings

CONTROLLED RELEASE GRANULES

RELATED APPLICATIONS

This application is a continuation-in-part of my co-pending application U.S. Ser. No. 114,729, filed Feb. 7, 1980, which is in turn a continuation-in-part of application U.S. Ser. No. 018,528, filed Mar. 8, 1979, both are now abandoned.

BACKGROUND OF THE INVENTION

Methyl-2-(dimethylamino)-N-[[methylaminocarbonyl]oxy]-2-oxo-ethanimidothioate, hereafter referred to by the common name oxamyl, is extremely effective as a contact type, broad spectrum insecticide and nematicide. It is especially useful in pre-plant soil incorporation treatment.

The long-term insecticidal and nematicidal performance of oxamyl is impaired by its disappearance in soil, a problem believed to be accelerated by rainfall, aeration, sunlight, alkalinity and elevated temperatures. This instability was discussed by J. Harvey, Jr. and J. C-Y Hau, Agricultural and Food Chemistry, Vol. 26, No. 3, page 536 (1978). Also, water leachability is a major problem, especially in sandy soils, due to the high solubility of oxamyl in water, about 20% at 25° C. Thus, in heavy rainfall, oxamyl could be diluted to a sub-effective level for nematodes or simply be washed away. Another problem relating to oxamyl use is the handling safety of oxamyl as it has high toxicity, exemplified by an $LD_{50}$ rating of of 5.4 mg/kg.

These problems could conceivably be eliminated or at least reduced by providing an effective barrier for an oxamyl formulation. Such a barrier should strike the critical balance between gradually releasing sufficient oxamyl to control nematodes while at the same time holding in reserve oxamyl that would be lost to the environment due to factors cited above.

It is known to use slow-release systems for applying insecticides. One problem with such systems, however, is that they normally exhibit reduced early activity. This is due to the presence of the barrier material which reduces the availability of the insecticide.

There thus exists a need for prolonging the excellent insecticidal and nematicidal activity of oxamyl without impairing its initial activity. There is also a need for improving the handling safety of oxamyl.

SUMMARY OF THE INVENTION

According to the instant invention, controlled-release granules have been unexpectedly discovered which gradually release oxamyl in soil and greatly increase its residual insecticidal and nematicidal activity without significantly reducing its early activity. This granule also exhibits reduced mammalian toxicity.

The controlled-release granules of this invention consist essentially of particles of an inert carrier coated or impregnated with an insecticidally or nematicidally effective amount of oxamyl and coated or impregnated with a barrier material. The barrier material consists of a paraffin wax admixed with up to about 50% by weight of a modifier or combination of modifiers selected from low molecular weight oxidized polyethylenes, ethylene copolymers containing up to about 40% of vinyl acetate comonomer, and polyterpenes. The barrier material must have a water absorption rate of no greater than about 0.2% when measured for ⅛" specimen in water at 73.4° F. for 24 hours. These granules are capable of releasing oxamyl in pure water at 20° C. at a rate of no more than 80% in four hours.

DETAILED DESCRIPTION OF THE INVENTION

The granules of the invention are made from an inert carrier. The term inert describes a material which will not interact with the oxamyl and which is practically insoluble in water. A preferred carrier is fused attapulgite, such as "Florex LVM" made by the Floridin Company. Other types of carriers which may be utilized include other attapulgites, diatomaceous earth, silicas, kaolinites, montmorillonites, calcium carbonates, talcs, crushed brick, ground shell corncob and prophyllites. When the more porous carriers such as the diatomaceous earths are used, the granules will be impregnated with the oxamyl as well as the outer barrier material. On the other hand, when less porous carriers such as the attapulgites are used, the oxamyl and the barrier are more likely to be on or near the outside of the granule.

The amount of oxamyl present in the granules ranges between about 1.0 and 20 weight percent, preferably about 5 and 15 weight percent, and most preferably about 10 percent. The final dry, controlled release granules contain about 4–30% barrier material, preferably about 20%. Optionally, they may contain other desirable adjuncts, for example, stabilizers for oxamyl or the polymer such as phosphoric acid, bactericides, and various coloring agents for showing the area treated. The granules may be regular or irregular in shape, and, in their largest linear dimension, are 300 to 5000 microns (50–4 mesh).

As previously mentioned, the granules of this invention should be capable of releasing oxamyl in pure water at 20° C. at a rate of no more than 80% in four hours. For some purposes, such as use in areas where extremely heavy rain is likely to occur, the release rate may preferably be no more than about 25% in four hours. The release rate may be easily measured by placing the granules in water at 20° C. for four hours. The amount of granules and water used should be sufficient to produce a 3.5% oxamyl solution if all the oxamyl were to be released. The amount of free oxamyl in the water phase is determined by comparing index of refraction measurements with those for known oxamyl solutions. Alternatively, spectrophotometric methods can be used such as ultraviolet or infrared absorption.

Barrier materials which are useful for preparing the slow-release granules of this invention are those which exhibit a water absorption rate of no greater than about 0.2% when measured according to ASTM Test D-570. This test, which is known to those skilled in the art, is described in the 1967 Book of ASTM Standards, the disclosure of which is herein incorporated by reference. Absorption rate figures for various barrier materials are available in the Modern Plastics Encyclopedia, 1979-80 Edition, the disclosure of which is incorporated by reference. Briefly summarized, Test D-570 is as follows:

ASTM TEST D-570

A specimen, ⅛ in. thick, is dried 24 hours in an oven at 50° C., cooled in a desiccator and immediately weighed. The specimen is then immersed for 24 hours in water at 73.4° F. Upon removal, the specimen is wiped dry with a cloth and immediately weighed. Increase in weight is reported as percent gained. For materials which lose some soluble matter during immersion, the sample must be re-dried, re-weighed, and reported as "percent soluble matter lost." The percent gain in weight plus percent soluble matter lost equals percent water absorption.

The paraffin wax barrier material of this invention is modified with up to about 50%, preferably about 25 to 50%, of a modifier or combination of modifiers selected from low molecular weight (e.g., about 2000 to 5000) oxidized polyethylenes, ethylene copolymers containing up to about 40% of vinyl acetate comonomer and polyterpenes. The polyterpenes preferably have a melt viscosity of about 100 poises at 130° to 160° C. These modifiers serve to increase the softening temperature of the wax and to improve its toughness.

The more preferred barrier material is paraffin wax admixed with oxidized polyethylene in a weight ratio of approximately 1:1. Granules made using this preferred barrier material provide highly effective controlled release of oxamyl. These granules surprisingly also do not tend to aggregate during preparation or storage, thereby making it easier to prepare flowing, uniformly, sized granules, a feature which aids in the accurate and facile application of the pesticide.

The granules of this invention may be prepared by any of a number of processes. The preferred processes are generally described as follows:

(a) An inert carrier is first contacted with a solution of an effective amount of oxamyl. Suitable solvents include water, acetone, methanol or mixtures thereof, and the halogenated alkanes, such as methylene chloride. Next the solvent is removed, and the carrier is contacted with a melt of the barrier material followed by cooling.

(b) An inert carrier is contacted with finely divided oxamyl. After the insecticide is uniformly distributed over the surface of the inert mineral granule the product is contacted with a melt of the barrier material followed by cooling.

The application of the barrier material to the granule in a melt rather than in a solution is advantageous because the need for a polymer solvent is avoided. This greatly simplifies the process and improves handling safety. One skilled in the art would know how to carry out the steps recited in the description of processes (a) and (b). A preferred method for contacting the carrier with the oxamyl consists of spraying the solution, onto granules which are being mechanically tumbled in a ribbon blender or rotating mixer. Alternatively, the solution, may be applied to granules which are agitated in an air stream using conventional fluidized bed equipment.

The barrier material may then be applied to the oxamyl-containing granules while they are being mechanically agitated. This can be done in a ribbon or paddle blender. It is often advantageous to preheat the granules before melt-coating to avoid premature solidification of the polymer melt and, thereby, to improve the uniformity of coverage. Where the oxamyl granules are preheated, it is sometimes preferable to add the barrier components as particulate solids in order to avoid the need for a separate melt mixer. Slight agitation of the granules during cool-down can help prevent agglomeration.

The preparation and utility of the pesticidal granules of this invention are illustrated in the following examples.

EXAMPLE 1

70.0 g Florex LVM® 8-16 mesh granules (fused attapulgite made by the Floridin Company) were coated with 41.7 g Vydate®L (Du Pont formulation containing 24% oxamyl). Solvent was removed by air drying in a laboratory hood.

EXAMPLE 2

8.0 g of the granules of Example 1, heated to 80°, were treated with 2.0 g of a melt mixture of paraffin wax (Gulfwax®, Gulf Oil Corporation) and oxidized polyethylene (Epolene® E-10, Eastman Chemical Products, Inc.) heated to 105° with hand agitation. The product was held at 95° for 10 minutes with periodic hand stirring. The granules were agitated slightly during cooling down giving unagglomerated, free-flowing controlled release oxamyl granules containing 10% oxamyl and 20% barrier. The release rate in water at 20° was 15.0% in 4 hours.

EXAMPLE 3

The process of Example 2 was repeated except for the use of 10.0 g powdered oxamyl instead of Vydate®L in the first step. The product had a composition similar to that of Example 2 except that the release rate was 57% in 4.0 hours.

EXAMPLE 4

The process of Example 2 was repeated except for the use of 16-30 mesh fused attapulgite granules as an inert mineral base instead of 8-16 mesh granules. The release rate was 26% in 4 hours.

EXAMPLE 5

This example is presented to illustrate a controlled release oxamyl granule system that does not meet the stringent barrier requirements set forth above and, consequently, as shown in Table I below, does not perform as well as products of the type described in Examples 2-4. Celatom® MP-78, diatomaceous earth granules, (Celatom® MP-78, Eagle-Picher Industries) (15.88 kg) were coated with 8.06 kg Vydate®L. The resultant granules were dried in an air oven at 45° C. and then coated with a solution of 1.55 kg polystyrene (Shell® 314) in 10.0 l of toluene. The toluene was removed in a vacuum oven at 45° giving a product containing 10% oxamyl and 8% polystyrene as an overcoat. This product released 83% of its oxamyl in 4.0 hours in water at 20° C. In attempts to use additional polystyrene, for reduced release of oxamyl, some agglomeration of the granules occured during drying.

EXAMPLE 6

In field tests, granules of the type described in Example 2 showed outstanding performance in controlling nematodes in sweet corn, carrots and cabbage plots. These controlled-release oxamyl granules performed best relative to other treatments, especially during periods involving heavy rainfall, as shown in Table I.

TABLE I

| | Sweet Corn | |
|---|---|---|
| Treatment* | Average Number of Ears per Plot | Average Weight of Corn From Plot |
| Untreated | 9.0 | 5.4 |
| Vydate® 10G granules | 9.8 | 5.8 lbs. |

TABLE I-continued

| | | |
|---|---|---|
| Granules of Example 2 | 11.6 | 7.7 lbs. |
| Granules of Example 5 | 9.6 | 6.3 |

*Applied at a rate of 2 lb per acre in furrow plots of equal size at planting time over seeds; there were 3 days of rainfall over 2" during the test period (2 months).

| Treatment* | Carrots % Yield Increase |
|---|---|
| None | 0 |
| Vydate ® 10G | 100 |
| Granules of Example 2 | 271 |
| Granules of Example 3 | 186 |

*Preplant incorporated, seeded 2 weeks after treatment at rate of 4 lb/acre, 1 day of rainfall over 2" during test period (3.3 months).

Similarly, the yield of cabbage was highest with granules of Example 2 with an increase of 27% over the case of no treatment using a treatment rate of 4 lb/acres. The test period involved over 2" of rainfall over a six-day period.

In a separate test designed to evaluate the early performance of the granules of Example 2, nematode control was evaluated after only two weeks in comparison with the control, at a rate of only 0.25 kg/ha rate. The peformance of the product of Example 2 and the commercial Vydate ® 10G control containing no barrier were substantially equal, i.e., over 95% control.

What is claimed is:

1. An insecticidal or nematicidal granule consisting essentially of particles of an inert carrier impregnated or coated with an effective amount of oxamyl and coated or impregnated with a barrier material, said barrier material having a water absorption rate of no greater than about 0.2% when measured for $\frac{1}{8}$" specimen in water at 73.4° F. for 24 hours, and said granule being capable of releasing oxamyl in water at 20° C. at a rate of no more than 80% in 4 hours, said barrier material consisting essentially of paraffin wax admixed with up to about 50% of a modifier or combination of modifiers selected from low molecular weight oxidized polyethylenes, ethylene copolymers containing up to about 40% of vinyl acetate comonomer and polyterpenes.

2. The composition of claim 1 where the modifier is a low molecular weight oxidized polyethylene.

3. The composition of claim 1 where the modifier is an ethylene copolymer containing up to about 40% of vinyl acetate comonomer.

4. The composition of claim 1 where the modifier is a polyterpene.

5. The composition of any of claims 1 to 4 where the paraffin wax is admixed with about 25 to 50% of a modifier or combination of modifiers.

6. The composition of claim 2 where the paraffin wax and the low molecular weight oxidized polyethylene are present in a weight ratio of approximately 1:1.

7. The composition of claim 1 where the inert carrier is fused attapulgite.

8. The composition of claim 1 which contains about 4 to 30% by weight of barrier material.

9. The composition of claim 8 which contains about 20% by weight of barrier material.

* * * * *